(12) United States Patent
Boyer et al.

(10) Patent No.: US 10,334,351 B2
(45) Date of Patent: Jun. 25, 2019

(54) HEADSET SYSTEM

(71) Applicant: Team IP Holdings, LLC, Grand Prairie, TX (US)

(72) Inventors: Gary Boyer, Bella Vista, AR (US); Timothy D. Schnell, Rancho Santa Fe, CA (US)

(73) Assignee: Team IP Holdings, LLC, Grand Prairie, TX (US)

( * ) Notice: Subject to any disclaimer, the term of this patent is extended or adjusted under 35 U.S.C. 154(b) by 0 days.

(21) Appl. No.: 15/913,743

(22) Filed: Mar. 6, 2018

(65) Prior Publication Data
US 2018/0262825 A1    Sep. 13, 2018

Related U.S. Application Data

(60) Provisional application No. 62/468,271, filed on Mar. 7, 2017.

(51) Int. Cl.
*H04R 1/10* (2006.01)
*A61F 11/14* (2006.01)
*H04R 5/033* (2006.01)

(52) U.S. Cl.
CPC ............. *H04R 1/105* (2013.01); *A61F 11/14* (2013.01); *H04R 1/1041* (2013.01);
(Continued)

(58) Field of Classification Search
CPC ...... H04R 1/10; H04R 1/1008; H04R 1/1066; H04R 1/105; H04R 1/1041; H04R 1/1083;
(Continued)

(56) References Cited

U.S. PATENT DOCUMENTS 5,406,037 A * 4/1995 Nageno ................ H04R 5/0335
181/129
5,574,795 A * 11/1996 Seki ..................... H04R 5/0335
381/370
(Continued)

OTHER PUBLICATIONS

Tyll Hertsens, "Philips Citiscape Downtown", Feb. 13, 2012, InnerFidelity, pp. 1-5.*
(Continued)

*Primary Examiner* — Thang V Tran
(74) *Attorney, Agent, or Firm* — Knobbe, Martens, Olson & Bear, LLP (57) ABSTRACT

Apparatus and methods for headsets, such as multi-source audio amplification and ear protection devices, are provided herein. In certain configurations, protection headset system includes a removable growth band that fills the gap of the user and a headband of the device. The device may optionally have at least one microphone that generates an ambient sound signal based on detecting ambient sound, at least one speaker, and an electrical system that controls sound outputted by the at least one speaker based on amplifying the ambient sound signal and a secondary sound source signal. The electrical system receives a user-controlled volume signal that is operable to control an amount of amplification provided to the ambient sound signal, and/or an amount of amplification provided to the secondary sound source signal.

21 Claims, 6 Drawing Sheets

(52) U.S. Cl.
CPC ......... *H04R 1/1083* (2013.01); *H04R 1/1008* (2013.01); *H04R 5/0335* (2013.01); *H04R 2201/107* (2013.01); *H04R 2430/01* (2013.01)

(58) Field of Classification Search
CPC .......... H04R 2201/10; H04R 2201/107; H04R 5/0335; H04R 2430/01; A61F 11/14
See application file for complete search history.

(56) References Cited

U.S. PATENT DOCUMENTS

| | | | | |
|---|---|---|---|---|
| 5,590,213 | A * | 12/1996 | Urella | H04R 5/0335 381/370 |
| 2014/0192994 | A1* | 7/2014 | Chen | H04R 1/1083 381/71.6 |
| 2016/0050486 | A1* | 2/2016 | Uggla | H04R 1/1091 381/378 |
| 2016/0295313 | A1* | 10/2016 | Martin | H04R 1/1041 |
| 2017/0318371 | A1* | 11/2017 | McAllister | H04R 1/1058 |

OTHER PUBLICATIONS

Baby Banz Earmuffs Infant Hearing Protection on Amazon.com <https://www.amazon.com/Baby-Earmuffs-Infant-Hearing-Protection/dp/B007BEHSDU/ref=pd_sbs_75_1?_encoding-UTF8&pd_rd_i=B007BEHSDU&pd_rd_r=FYT2RF64QG7PKNBBH834&pd_rd_w=g0kuc&pd_rd_wg=IEx56&refRID=FYT2RF64QG7PKNBBH834&th=1> (printed Mar. 6, 2018).

* cited by examiner

HEADSET SYSTEM

CROSS-REFERENCE TO RELATED APPLICATIONS

This application claims the benefit of U.S. Provisional Application No. 62/468,271, filed Mar. 7, 2017, and titled HEADSET SYSTEM, the entire contents of which are hereby incorporated by reference and should be considered a part of this specification. This application is related to U.S. application Ser. No. 15/212,129, filed Jul. 15, 2016, the entire contents of which are hereby incorporated by reference and should be considered a part of this specification.

BACKGROUND

Field

The described technology generally relates to infant headset assemblies.

Description of the Related Technology

Headset assemblies can be used for a variety of purposes. For example, an audio headset can assist in hearing by amplifying sound from a single audio source, thereby allowing the user to listen to the audio source at a desired volume level. The headsets can be also used to protect a user's ears from damage in loud environments. Such headsets can be particularly useful for protecting infants whose auditory bones and tissues are still developing. To maximize the benefit of using such headsets, it would be important to choose headsets that fit each individual infant's head well. However, finding headsets for infants with suitable size and fit can be both challenging and costly, partly because of the rapid growth of an infant's head.

SUMMARY

There is a need for a headset device that can accommodate an infant's rapidly growing head. The headset device can allow a user to selectively hear sounds, such as an ambient sound source captured via microphone(s) while optionally also hearing sounds from a secondary audio source, such as audio received from a wireless connection (for example, BLUETOOTH®), a wired connection (for example, an audio input port), and/or a built-in audio component (for instance, a music player). In some embodiments, the headset device can be a multi-source audio amplification and ear protection device. Apparatus and methods for such multi-source audio amplification and ear protection devices are well described in U.S. application Ser. No. 15/212,129.

The headset device can be used in a wide variety of applications, and can be useful for infants. In one example, infants may use the headset device as headphones for selectively playing a prerecorded music, lullabies, or soothing white noises. At the same time, the headset can allow the infant user to selectively also hear ambient sounds such as a voice of a parent. Additionally, the device can protect the infants from noises in loud places like concerts or stadiums.

However, the use of headsets, such as a multi-source audio amplification and ear protection device on infants may be challenging. For the effective control of volume by the headset and proper limitation of noise, a secure and stable fit of the headset device on the head and ears of the infant would be required. Further, a secure and stable fit would be desirable for the comfort of the infant. However, due to the rapid growth of infants, it would be difficult to find a headset that would continuously fit well on the infant user as the user grows up. Additionally, purchasing new headsets as the infants grow would be costly. To resolve these issues, one aspect of the present invention provides an audio amplification and ear protection device, in a form of headset, which can securely and stably fit on an infant's growing head, so that it can be used on the infant user for an extended period of time as the infant grows.

An audio amplification and ear protection device can be implemented in a wide variety of form factors (e.g., in-ear buds, on-ear or over-ear cups/muffs) and can include a wide range of features and functionality.

In accordance with one aspect of the invention, a headset system (e.g., audio headset system) is provided that can fit wide range of size of heads, so that the system can fit infants' heads as they grow.

In another aspect, an audio headset system is provided that is adjustable in size and that can be accommodate an infant's head as his or her head continues to grow.

In accordance with another aspect, an infant headset system is provided. The infant headset system comprises a headset comprising a left ear speaker (e.g., as part of a left ear cup), a right ear speaker (e.g., as part of a right ear cup) and a headband that interconnects the left and right ear cups. The system also comprises a fabric band comprising a pair of straps attached to opposite ends of a central band portion. Each of the pair of straps extends between a first end and a second end and is attached to the central band portion at a location along the strap between the first and second ends (e.g., forming generally H-shape when the fabric band is laid generally flat). The pair of straps is configured to removably wrap at least partially about the headband at two locations of the headband (e.g. with hoop and loop fasteners) to couple the fabric band to the headband so that the central band portion extends below the headband so that the central band portion is disposed between the headband and the user's head when in use. The band may be configured to fill a space between the headband and the user's head when in use to facilitate the secure and stable fit of the headset over the infant's head to accommodate the infant's growing head, so that the left and right ear cups are positioned on the infant's ears. The central band portion of the band may have a width generally equal to a width of the headband, and/or comprise a resilient material that cushions the headband on the infant's head. The headset may provide passive noise suppression. The headset may comprise a computer readable memory and has one or more pre-recorded sounds saved on the memory, the headset being actuatable to play the one or more pre-recorded sounds. The headset may comprise electronics configured to filter out ambient sounds above a predetermined decibel level.

In accordance with another aspect, an infant headset kit is provided. The kit comprises a headset comprising a left ear speaker (e.g., as part of a left ear cup), a right ear speaker (e.g., as part of a right ear cup) and a headband that interconnects the left and right ear cups. The kit further comprises one or more bands comprising a pair of straps attached to opposite ends of a central band, each of the pair of straps extending between a first end and a second end and attached to the central band at a location along the strap between the first and second ends, the pair of straps configured to releasably couple the fabric band to the headband so that the central band portion extends below the headband so that the central band portion is disposed between the headband and the infant's head when in use. The one or more bands may be reversible. The kit may include a plurality of bands having a central band portion of different thickness. The headset may provide passive noise suppression. The headset may have one or more pre-recorded sounds saved on the memory, the headset being actuatable to play the one or more pre-recorded sounds. The headset may comprise electronics configured to filter out ambient sounds above a predetermined decibel level.

In accordance with another aspect, an infant headset system is provided. The infant headset system comprises a headset comprising a left ear speaker, a right ear speaker, and a headband that interconnects the left and right ear speakers. The system further comprises a band comprising at least one strap and a body portion, the strap configured to releasably couple the band to the headband so that the body portion of the band is disposed between the headband and a user's head when in use. The body portion of the band comprises a compressible, resilient material.

In accordance with another aspect, an infant headset system is provided. The infant headset system comprises a headset comprising a left ear speaker, a right ear speaker and a headband that interconnects the left and right ear speakers. The system further comprises a growth band supported by the headband and comprising a body portion so that the body portion is disposed between an underside of the headband and a user's head when in use. There may be a spacing between the headband and the body portion when the headset is not worn by the user, and the body portion may be movable towards the headband in response to urging from the user's head when the headset is in use, resulting in a reduction in the spacing between the headband and the body portion. The body portion of the growth band may not be attached to the headband and the growth band may be optionally attached to the headband at first and second ends of the growth band. The growth band may be fixedly or releasably attached to the headband. The body portion of the growth band may comprise a compressible, resilient material.

BRIEF DESCRIPTION OF THE DRAWINGS

Example implementations disclosed herein are illustrated in the accompanying schematic drawings, which are for illustrative purposes only.

DETAILED DESCRIPTION

The following detailed description is directed to certain implementations for the purposes of describing the innovative aspects. However, the teachings herein can be applied in a multitude of different ways. As will be apparent from the following description, an audio amplification and ear protection device can be implemented in a wide variety of form factors (e.g., in-ear buds, on-ear or over-ear cups/muffs) and can include a wide range of features and functionality.

Headset

Figure 1A:
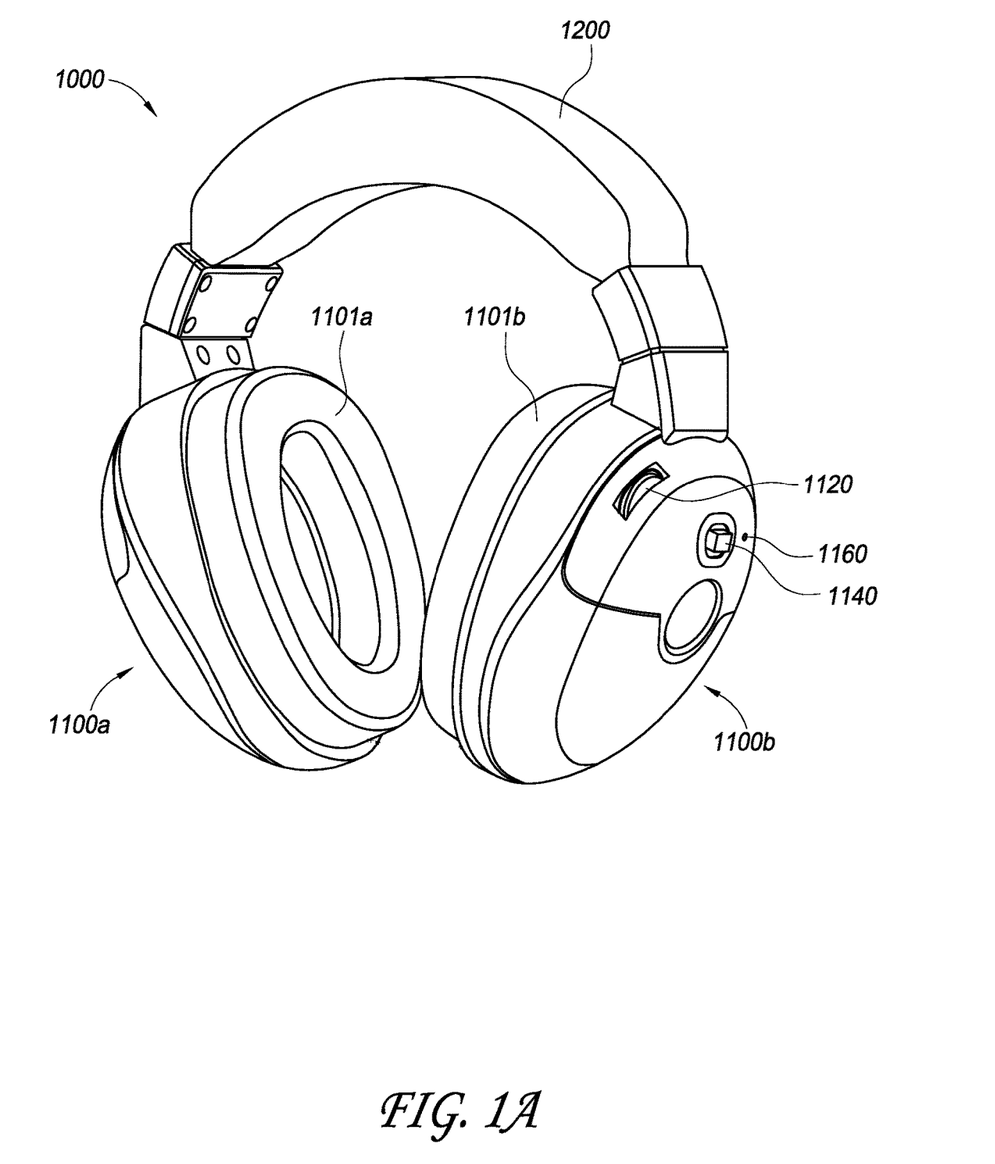
FIG. 1A is a front perspective view of a headset according to one embodiment.
Figure 1B:
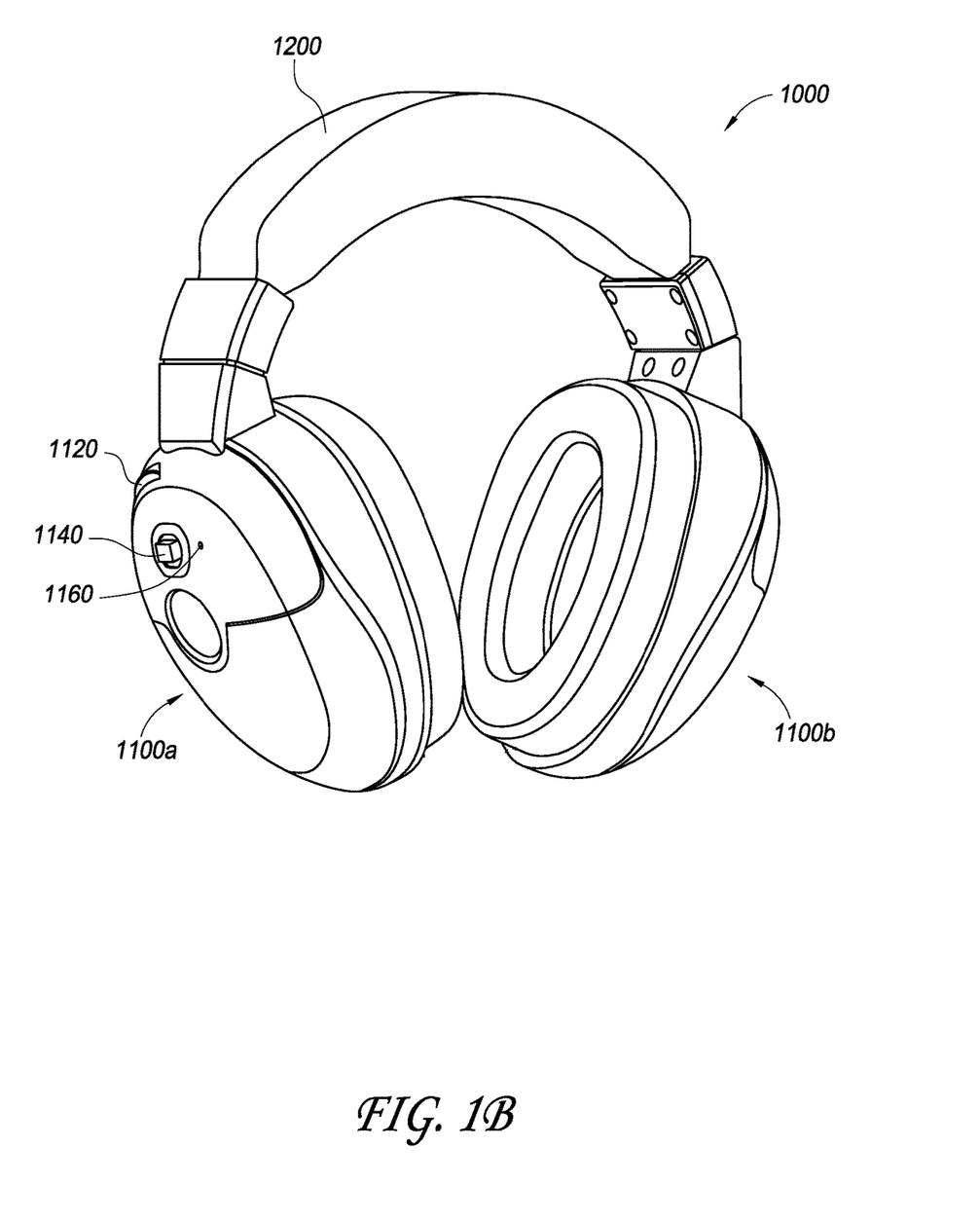
FIG. 1B is a rear perspective view of the headset of FIG. 1A.

FIGS. 1A-1B illustrate various views of one embodiment of an audio amplification and ear protection device or a headset 1000. The headset 1000 includes a first or right ear cup 1100a, a second or left ear cup 1100b, and a headband 1200 connecting the first or right ear cup 1100a and the second or left ear cup 1100b. In other embodiments, the ear cups may be replaced with ear plugs or any other suitable forms of ear pieces. The headset 1000 may be worn by the user by putting the ear cups 1100a and 1100b on the user's ears, while putting the headband 1200 over the head of the user so that the headband 1200 sits on the top of the user's head. In one embodiment, the ear cups 1100a, 1100b can sit on the ear. In another embodiment, the ear cups 1100a, 1100b can sit over the ear.

In some embodiments, the headband 1200 may include a smooth foam. In some embodiments, the width of the headset 1000 can be adjusted, for example, by retracting the ear cups 1100a, 1100b from the ends of the headband 1200 via its junction with ear cups 1100a and 1100b. However, the widthwise adjustability of the headband 1200 may be limited, and may not allow the headband 1200 to sit on the infant's head while the ear cups 1100a, 1100b are over the infant's ears, resulting in an insecure and unstable fitting that may cause the ear cups 1100a, 1100b to slide down past the infant's ears or may cause the headband 1200 to swing forward in front of the infant's head.

In some embodiments, the headset 1000 may include one or more microphones operable to capture ambient sound. For example, in the illustrated embodiment, the left ear cup 1100b includes a microphone 1160. In some embodiments, the right ear cup 1100a may include one or more microphones, and in some embodiments, both or none of the ear cups may include the microphones. In some embodiments, the microphone may be placed at the headband 1200. In some embodiments, the right and/or the left ear cups 1100a and 1100b may include speakers therein, such that speakers amplify sound signals from various sources, as described in further detail below. In some embodiments, the headset 1000 may include one or more control interfaces. For example, in the illustrated embodiment, the headset 1000 includes a volume control 1120 (e.g., volume control wheel or dial) and a button interface 1140 on the left ear cup 1100b. In some embodiments, the control interfaces, such as the volume control 1120 and the button interface 1140 may be placed at the left and/or the right ear cup 1100a/1100b or at the headband 1200.

Passive Ear Protection Device

In some embodiments, the ear protection device may include over-ear muff-type cups similar to 1100a and 1100b of FIGS. 1A-1B and a headband similar to 1200 of FIGS. 1A-1B. Such over-ear muff-type cups can provide a greater amount of ear protection and/or improved comfort for extended periods of time. For example, the cups 1100a and 1100b can be placed over the user's ears, thereby enclosing the user's ears and reducing the amount of ambient sound that directly reaches the user. In some embodiments, the cups 1100a and 1100a may include a foam material that absorbs and reduces the amount of ambient sound that reaches the user's ears. Thus, the headset device 1000 can be a passive device (e.g., exclude any electronics) suitable for a wide range of loud environments, including, but not limited to, traffic, playgrounds, shopping malls, theaters, etc. In one embodiment, the passive headset device 1000 and one or more removable growth bands 2000 described in this section or elsewhere in the specification can be provided as part of a kit, along with instructions for use.

Active Ear Protection Device

In some embodiments of the ear protection device or headset 1000, the ear protection device may compress and control ambient sound (e.g., via the operation of electronics in the headset 1000). When the headset device 1000 is activated, the ear protection device may compress the ambient sound to lower than certain decibel level, for example by filtering out sound above a certain decibel level (e.g., sounds greater than 75 db, sounds greater than 60 db, etc.), such that the device 1000 allows the user to hear normal conversational level of ambient sound while compressing loud noises. The device may optionally be selectively activated and/or deactivated, for example, by pressing a button such as the button interface 1140 shown in FIGS. 1A-B. In another implementation, the device 1000 is automatically activated to compress and control ambient sound (e.g., without requiring the user to press a button to initiate actuation). Even when the device is not activated, the ear protection device or headset 1000 may enclose the user's ears and reduce the amount of ambient sound that directly reaches the user, such as passive ear protection device described above. In some embodiments, the device 1000 may include an indicator which indicates the status of the device 1000. For example, in the illustrated embodiment, the button interface 1140 may change its color when the device 1000 is activated or deactivated (for sound compression or filtering of sound above a predetermined decibel level). In one embodiment, the active headset device 1000 and one or more removable growth bands 2000 described in this section or elsewhere in the specification can be provided as part of a kit, along with one or more batteries and/or instructions for use.

Audio Amplification and Ear Protection Device

In some embodiments, the audio amplification and ear protection device or headset 1000 can provide secondary or prerecorded sounds to the user while reducing and actively compressing the amount of ambient sound in the same manner as the ear protection devices described above. The device can allow control of volumes of the ambient sound and the secondary sound being provided by the headset device 1000. In some embodiments, the headset device 1000 may have a memory that can store one or more pre-recorded sound files (e.g., lullabies, natural sounds, parents' voice, white noise or the heartbeat of the mother) so that the device 1000 can play internally stored sound files. In further embodiments, the device may include a USB slot or connector that can receive a connector or USB drive to load prerecorded sounds into the headset (e.g., into the memory of the headset). Alternatively, the USB connector can allow an external device to be connected to the headset device 1000 to provide the sound files. In one embodiment, the audio amplification and ear protection device or headset 1000 and one or more removable growth bands 2000 described in this section or elsewhere in the specification can be provided as part of a kit, along with one or more batteries and/or instructions for use.

Although FIGS. 1A-1B show one embodiment of an audio amplification and ear protection device that can provide a user with control of multiple audio sources, the teachings herein are applicable to a wide variety of configurations. For example, the teachings herein are applicable to audio amplification and ear protection devices implemented using a wide variety of form factors and/or including a wide range of features or functionality. Additionally, although shown as including ear cups, an audio amplification and ear protection device can include a wide range of ear piece(s), including, for example, ear plug(s), ear cup(s), ear phone(s), or a combination thereof. Further, some embodiments of an audio amplification and ear protection device may not include all parts shown in FIGS. 1A-1B, or may include additional features not shown in FIGS. 1A-1B.

The illustrated embodiment includes over-ear muff-type cups 1100a and 1100b, which can provide a greater amount of ear protection and/or improved listening and comfort for long periods. For example, the cups 1100a and 1100b can be placed over the user's ears, thereby enclosing the user's ears and reducing the amount of ambient sound that directly reaches the user. In some embodiments, the cups 1100a and 1100b may include foam material that is configured to absorb and reduce the amount of ambient sound to which the user's ears are exposed. Thus, the device 1000 can be suitable for a wide range of loud environments.

In the illustrated embodiment, the volume control (e.g., wheel) 1120 provides a user of the device 200 with control over the volume of ambient sound captured by the microphone 1160 and/or the volume of sound from a secondary sound source, which can be, for example, audio file stored internally in the memory of the device, received over a wireless connection (for instance, a BLUETOOTH®, Zigbee, Wi-Fi, NFMI, AirPlay, SKAA, 2.4 GHz RF, and/or other connection), audio received over a wired connection (for instance, via an audio input port), and/or audio received from a built-in audio component, such as a music player, an integrated radio (for instance, AM, FM and/or XM radio), integrated phone and/or audio playback device.

In some embodiments, each of the left ear cup 1100b and the right ear cup 1100a may include a volume control (e.g., wheel) and microphone, and the left-side volume control wheel can be operated (e.g., rotated) to control the volume of ambient sound captured by the left-side microphone, and the right-side volume control) can be operated (e.g., rotated) to control the volume of ambient sound captured by the right-side microphone. Accordingly, the volume of ambient sounds can be separately controlled to the left and right ears, in this embodiment.

Although the illustrated embodiment uses wheel interfaces implemented on the device 1000, the teachings herein are applicable to devices controlled in a wide variety of ways. For example, an ambient sound control interface and/or a secondary sound source control interface can use a different style of interface and/or can be located in other positions. Additionally, the teachings herein are applicable to devices that are remotely controlled, including but not limited, devices controlled using a dedicated remote control (wireless and/or wired, such as pluggable) and/or by using a tablet, phone, smart watch, laptop, computer, and/or other control device. Moreover, the teachings herein are applicable to devices that operate using voice-activated control. Furthermore, the teachings herein are applicable to devices that can be controlled in multiple ways, such by a combination of on-device interface(s), remote control device(s), and voice-activated control, thereby providing the user with flexibility in controlling the device in a manner that is desirable for a particular application.

In the illustrated embodiment, the volume control wheel 1120 is placed inside the ear cup and only partially exposed, lowering the chance of inadvertently adjusting and/or damaging the control wheel. Additionally, the wheel 1120 optionally includes a ribbed edge distributed around the circumference of the wheel, thereby facilitating gripping and turning of the wheel 1120. In some embodiments, the volume control wheel 1120 can be pressed in addition to being rotated to provide an additional input mode to the user of the device 1000. For example, pressing the wheel 1120 causes the device 1000 to toggle between different sounds from a secondary sound source (e.g., white noise, heartbeat, nature sounds, etc.).

In some embodiments, the two ear cups 1100*a* and 1100*b* can separately detect external, ambient noise from outside and separately transmit (or cancel) the noise to the respective ear. In some embodiments, each of the cups includes one or more microphones. For example, one or more microphones can be included and positioned to capture the user's voice, such as when the user is providing a voice command and/or using the device 1000 to make a call.

Including multiple microphones on the device 1000 can aid in capturing sounds at a wide variety of angles, including, for instance, 360 degrees around a user. Thus, while the microphones can be used to detect the same sounds, each microphone can face a different direction and provide a more accurate detection of the noise. For example, the microphones closer to the front of the user can detect noise coming from the front, and the microphones closer to the back of the user can detect the noise coming from the back. Similarly, the microphones closer to the right of the user can detect noise coming from the right, and the microphones closer to the left of the user can detect the noise coming from the left. The sounds can be communicated or reproduced to the speaker(s) of each ear cup 1100*a* and 1100*b* such that the user can better discriminate which direction sounds are coming from. For instance, if a turkey gobbles to the right of the user, the right-side speaker would reproduce the sound at a higher volume level relative to the left-side speaker. In some embodiments, each ear cup 1100*a* and 1100*b* includes two or more speakers. In one example, separate speakers are provided for sound captured from each microphone of the device. Thus, if a sound is generated behind and to the right of the user, a corresponding speaker would play the sound at a higher volume than the other speaker.

The audio amplification and ear protection device 1000 simultaneously processes both sounds from an ambient sound source and sounds from a secondary sound source, and allows the user to separately control the volume of the sounds. In one embodiment, the secondary sound source is provided from a wireless connection, such as a BLUETOOTH® connection. Other implementations, however, are possible. Thus, the device 1000 can be paired to another device, such as a smartphone, a tablet, a computer, and/or any other suitable electronic device. The paired device (e.g., a cell phone) can transmit audio signals such as music, dialog, or electronic notifications, which can be played in the speakers of the ear cups. The pairing can be activated for a device when the user presses a pairing button. In some embodiments, the button interface 1140 operates as the pairing button. The pairing can be performed in a variety of ways, including but not limited to, using the pairing button and/or via automatic pairing. In the illustrated embodiment, sounds from the secondary sound source can be played in the same speakers as ambient sounds detected by the device's microphones. However, other implementations are possible, such as configuration in which separate speakers are included for outputting the audio received from the secondary sound source.

The audio amplification and ear protection device 1000 includes an electrical system housed therein. In one implementation, each of the ear cups 1100*a* and 1100*b* includes electronic circuitry for processing sounds detected from the microphones of the cup and for driving the speaker of the cup. Electronics used for processing sounds from a secondary sound source can be implemented in a wide variety of ways, including, for example, in one or both of the cups. In the illustrated embodiment, the right ear cup 1100*a* is electrically connected to the left ear cup 1100*b* via a wire concealed in the headband 1200 in this example. In another embodiment, the right ear cup 1100*a* and the second ear cup 1100*b* each include a transceiver and communicate to one another wirelessly. In yet another embodiment, the right ear cup 1100*a* and the left ear cup 1100*b* communicate using a combination of wired and wireless signaling.

Additional details of the multi-source audio amplification and ear protection device 1000 can be as described herein.

Growth Band

Figure 2:
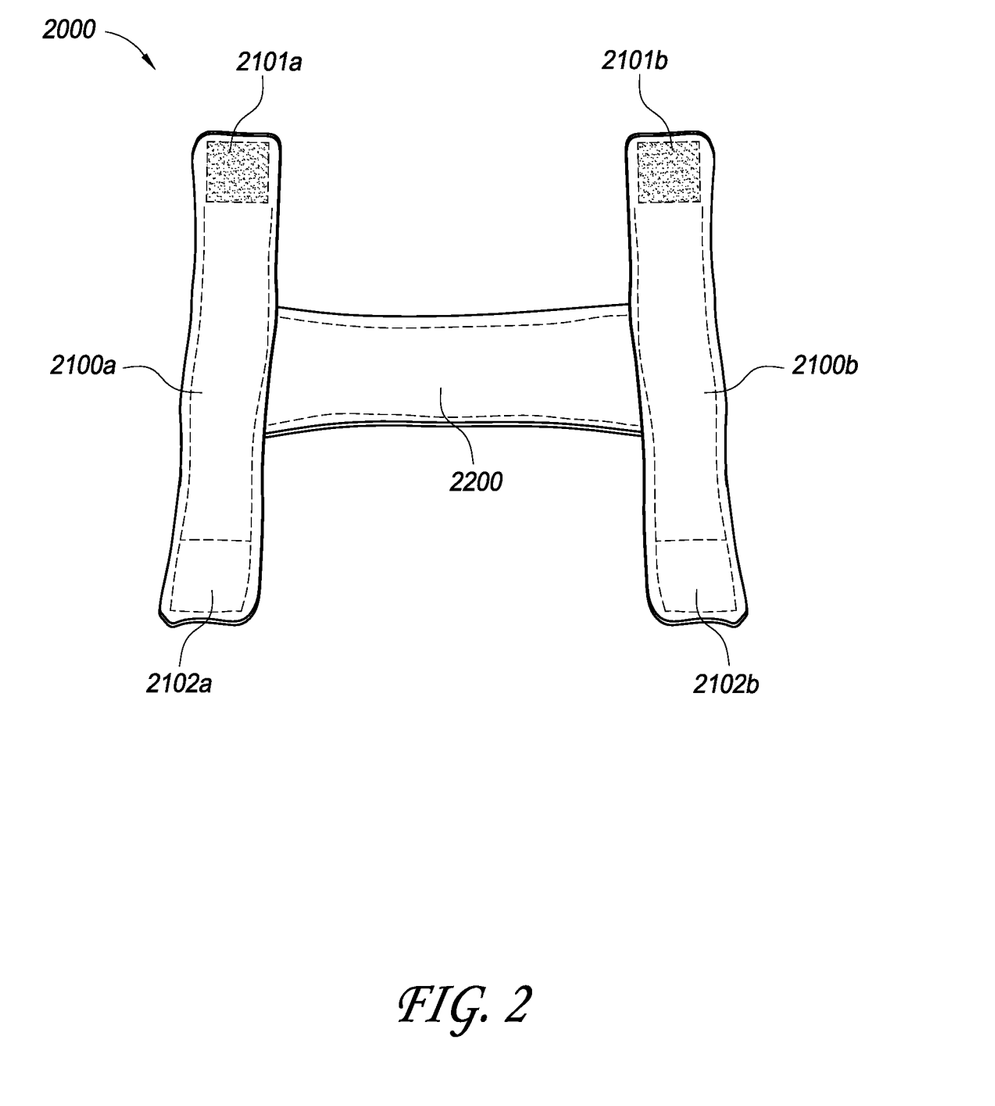
FIG. 2 illustrates a growth band according to one embodiment.

FIG. 2 depicts an embodiment of a removable growth band 2000 that can removably couple to the headband 1200, as discussed further below. The removable growth band 2000 can have a central band portion 2200 (e.g., a support band), a first strap 2100*a*, and a second strap 2100*b* (e.g., fastening straps). In some embodiments, the first strap 2100*a* and the second strap 2100*b* extend parallel to each other and are connected by the central band portion 2200. The straps 2100*a* and 2100*b* may extend perpendicularly to the central band portion 2200. In some embodiments, as such in FIG. 2, the length of the central band portion 2200 extends from the first strap 2100*a* to the second strap 2100*b* so that the removable growth band 2000 has H-shape when laid flat on a surface. In other embodiments, the band 2000 can have other shapes. In some embodiments, the straps 2100*a* and 2100*b* may be removable from the central band portion 2200. In such embodiments, the straps may be removably attached to the central band portion by means of VELCRO®, buttons, snaps, or any other suitable mechanisms. In other embodiments, the straps 2100*a* and 2100*b* are permanently fixed with the central band portion 2200 (e.g., sewn). In some embodiments, the growth band may further include a third strap between the first strap and the second strap (e.g., to secure a portion of the central band portion 2200 located between the first and second straps 2100*a*, 2100*b* to the headband 1200). In some embodiments, the growth band 2000 may have three or more straps. In some embodiments, the central band portion 2200 can have a greater width than the straps 2100*a*, 2100*b*. In another embodiment, the central band portion 2200 can have the same width as the straps 2100*a*, 2100*b*. In still another embodiment, the central band portion 2200 can have a smaller width than the straps 2100*a*, 2100*b*.

In some embodiments, at least a portion of the removable growth band 2000 can be flexible, allowing it to conform to the shape of the headband 1200 when coupled to the headset 1000, while able to lay flat (see FIG. 2) when detached from the headset 1000. The growth band 2000 can include a fabric material (e.g., cotton). In further embodiments, such fabrics may be machine-washable. In other embodiments, different parts of the growth band, for example, the straps 2100*a* and 2100*b*, and the central band portion 2200, can have different materials. In some embodiments, one side of the growth band 2000 may have different materials with the other side. For example, one side of the growth band 2000 may have a plusher material while the other side have a smoother material more resistant to stain or contamination, such that the side with the plusher material may contact the user's head and provide more cushion, while the side with the smoother material may contact the headband. In further embodiment, one side, for example, the side with smoother material may have a visual indicator such as a logo, to allow the user to distinguish sides with different materials and assemble the growth band with the headband in the correct orientation. In some embodiments, the growth band 2000 may include multiple layers of fabrics. In some embodiments, the fabrics may be infant-safe (e.g., hypoallergenic). In some embodiments, both sides of the removable growth band 2000 may have a fabric suitable for contact with the skin, so that the growth band 2000 is reversible.

In some embodiments, the central band portion 2200 may further include a resilient material disposed between two outer layers of fabric (e.g., between a top layer and a bottom layer of the central band portion 2200). In some embodiments, the resilient material can be a foam, a gel, cotton or any other suitable material or combinations thereof. In some embodiments, such resilient material is machine-washable. For example the portion of the growth band 200 that contact's the user's head can be constructed to be resilient and compressible (e.g., made of fabric and filled with cotton, foam, gel, or some other compressible, resilient material), providing increased comfort and to accommodate some amount of head growth. The thickness of the resilient material may vary, so that the thickness of the central band portion varies accordingly. In some embodiments, the thickness of the central band portion may be 0.5 cm to 10 cm. In some embodiments, the thickness of the central band portion may be 1 cm to 5 cm.

In some embodiments, each of the straps 2100a and 2100b may have at least one attachment element 2101a and 2101b and at least one receiving elements 2102a and 2102b, wherein the receiving elements can removably couple to the attachment elements. The attachment elements and the receiving elements can provide a temporary coupling, and can be mechanically pulled apart. In some embodiments, the at least one attachment elements and the at least one receiving elements are at opposite ends of a single strap 2100a, 2100b. For example, in some embodiments such as in FIG. 2, the straps 2100a and 2100b have attachment elements 2101a and 2101b, and receiving elements 2102a and 2102b, where attachment element 2101a can removably couple with receiving element 2102a and attachment element 2101b can removably couple with receiving element 2102b. In some embodiments, such the attachment elements and the receiving elements are in form of hoop-and-loop fasteners (such as VELCRO®), buttons, snaps, hooks, or any other suitable fastening mechanism. In some embodiments, the attachment elements and the receiving elements are effective after repeated washing of the growth band.

Figure 3A:
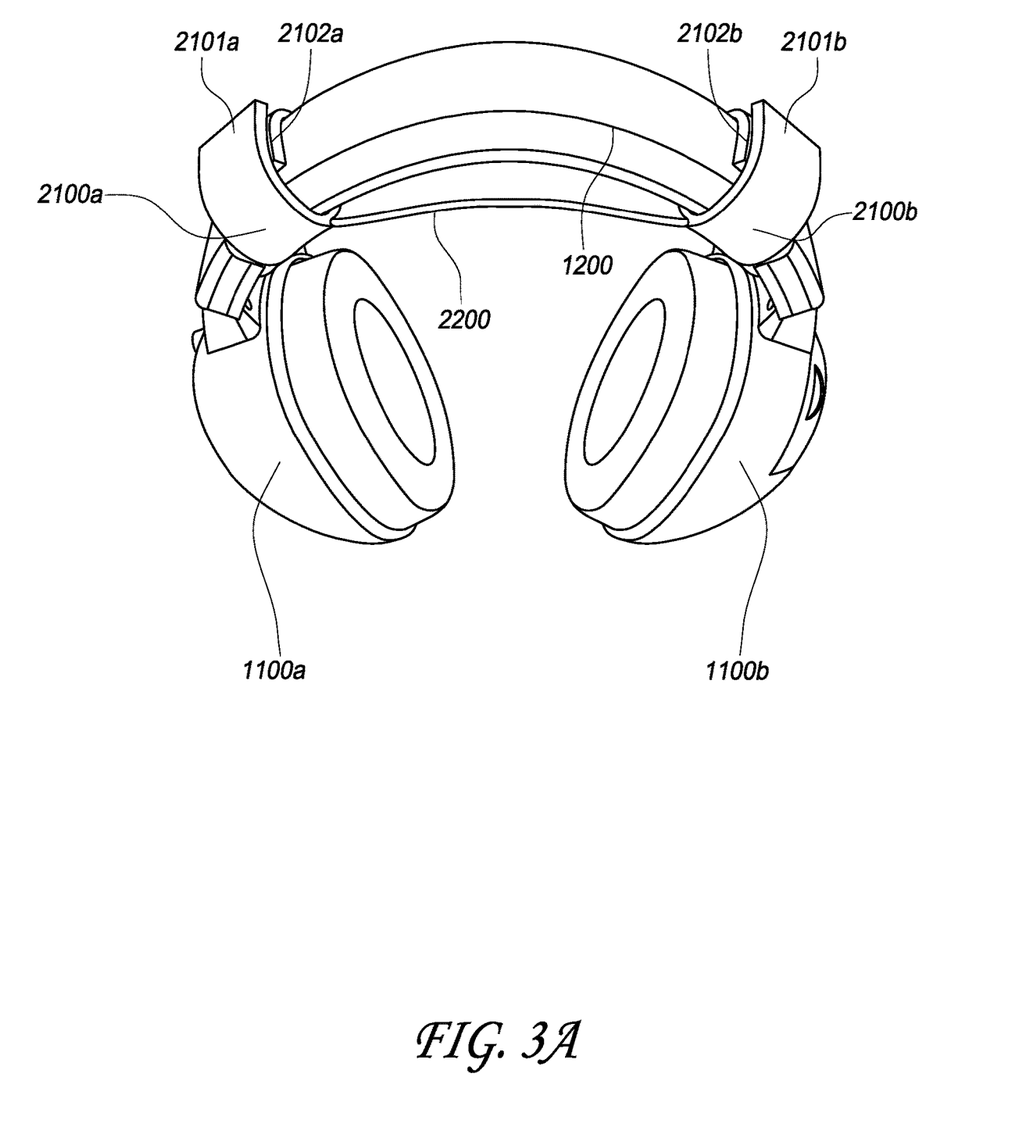
FIG. 3A is a top perspective view of another embodiment of a headset similar to FIG. 1A with the growth band of FIG. 2.
Figure 3B:
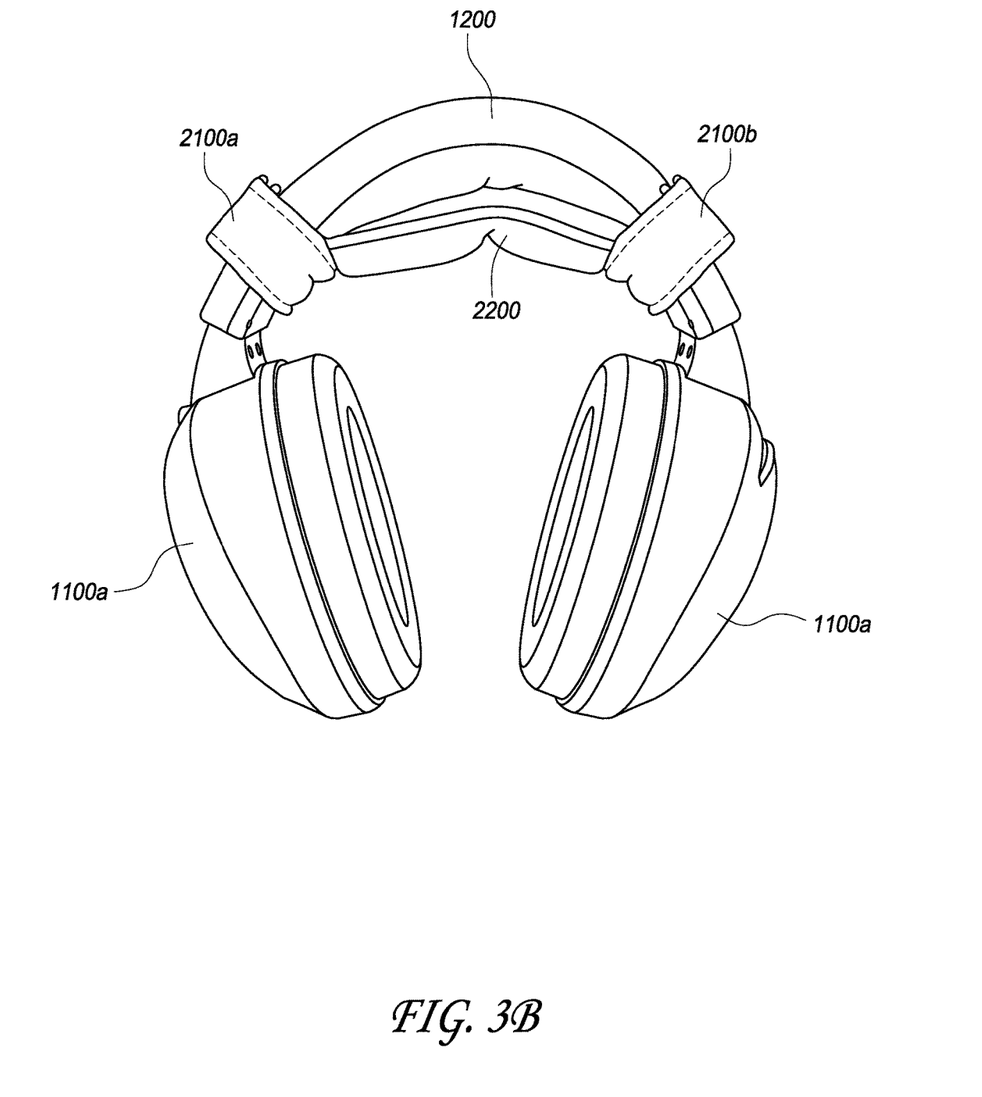
FIG. 3B is a front view of the headset of FIG. 3A.

The removable growth band 2000 may be removably or fixedly installed on headsets similar with those described in relation to FIGS. 1A and 1B. FIGS. 3A and 3B illustrates an embodiment of headset device 1000 with the growth band 2000 removably attached thereto. The growth band 2000 may be installed on the device 1000 by securing the straps 2100a and 2100b around the headband 1200. In some embodiments, the straps 2100a, 2100b may be removably secured by mating attachment elements 2101a and 2101b with corresponding receiving elements 2102a and 2102b respectively. In some embodiments, the central band portion 2200 may be aligned with the headband 1200 before securing the straps 2100a and 2100b around the headband 1200.

The growth band 2000 may be removed from the device 1000 by un-securing the straps around the head band 1200. In some embodiments, the straps can be unsecured by detaching the attachment elements 2101a, 2101b from the receiving elements 2102a, 2102b, for example, by application of force. In some embodiments, the attachment elements 2101a, 2101b and the receiving elements 2102a, 2102b can withstand multiple attachment and detachment cycles, so that the growth band 2000 can be installed and removed from the device 1000 as needed. In other embodiments (not illustrated) the growth band 2000 is fixedly attached to the headset 1200. For instance, the ends of the growth band 2000 or some other portion of the growth band 2000 can be sewn onto, form a part of, or be otherwise affixed to the headband.

As illustrated in FIGS. 3A-3B, the growth band 2000 may be supported by the headband 1200 so that the central band portion 2200 is disposed between an underside of the headband 1200 and a user's head (not shown) when in use. Therefore, the central band portion 2200 can advantageously facilitate the secure and stable fitting of the headset device 1000 on the head of the infant user even when the device 1000 is too large for the infant, for example by filling the gap between the infant's head and the headband 1200 of the headset device 1000. In some embodiments, the growth band 2000 can conform to the inner curve of the head band 1200. In further embodiments, the growth band 2000 can conform to the head of the infant, so that the central band portion 2200 contacts the infant's head and the headband 1200 during use. In some embodiments, the central band portion 2200 may not be attached to the headband 1200 while other parts of the growth band, for example, the first strap 2100a to the second strap 2100b are attached to the headband 1200. In some embodiments, the central band portion 2200 may suspend from the headband 1200 such that there may be a spacing between the headband 1200 and the central band portion 2200 when the headset is not worn by the user, and the central band portion 2200 may be movable towards the headband 1200 in response to urging from the user's head when the headset is in use, such that the spacing between the headband 1200 and the central band portion 2200 is reduced or completely removed, accommodating growth of the infant's head while maintaining comfort and a snug fit.

In some embodiments, the resilient material of the central band portion 2200 advantageously cushions the headband 1200 on the infant's head. In some embodiments, the central band portion 2200 is advantageously absorbent and absorbs, for example, perspiration on the infant's head. In some embodiments, the user may choose the growth band 2000 having an appropriate thickness, so that there is minimal space between the head band 1200 and the head of the infant. The user may change the growth band 2000 to a thinner one, or may completely remove the growth band as the head of the infant grows and the space between the head and the head band gets smaller. In some embodiments, the headset device 1000 can be packaged with multiple removable growth bands 2000 of varying thickness, so that the user may choose and install the appropriate growth band 2000 for the infant to use while wearing the headset device 1000.

The removable growth 2000 band may be coupled with any headsets that are similar to the headsets that are described in relation to FIGS. 1A-4C, or any other devices that the user may find suitable. For example, the removable growth band 2000 as described in this section or elsewhere in the specification may be coupled with any types of earmuffs or headphones described below.

Multi-Source Audio Amplification and Ear Protection Device

Figure 4:
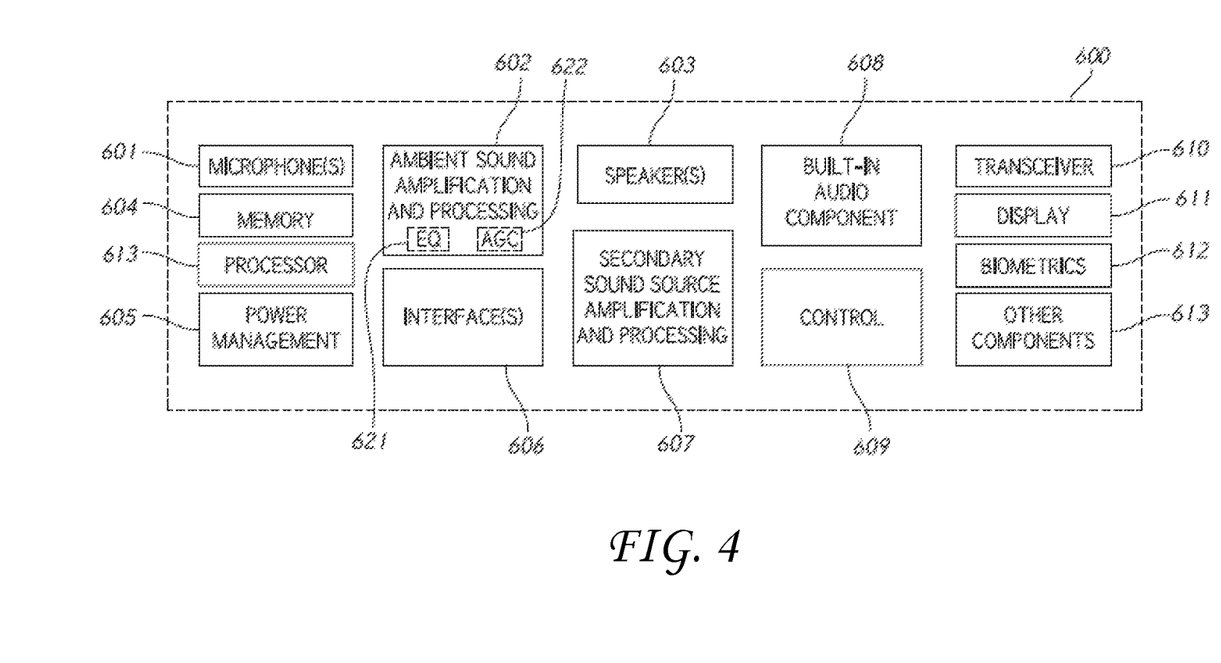
FIG. 4 is a schematic block diagram of a multi-source audio amplification and ear protection device according to one embodiment.

FIG. 4 is a schematic block diagram of a multi-source audio amplification and ear protection device 600 according to one embodiment. The multi-source audio amplification and ear protection device 600 includes microphone(s) 601, ambient sound amplification and processing circuitry 602, speaker(s) 603, memory 604, power management circuitry 605, user interface(s) 606, secondary sound source amplification and processing circuitry 607, a built-in audio component 608, control circuitry 609, an optional transceiver 610, an optional display 611, a biometrics component 612, and other components 613. As shown in FIG. 4, the ambient sound amplification and processing circuitry 602 includes frequency dependent processing circuitry 621 (equalization circuitry, in this example) and automatic gain control circuitry 622.

Although one example of components and functionality is shown in FIG. 4, a multi-source audio amplification and ear protection device can include more or fewer features. Moreover, a multi-source audio amplification and ear protection device can be implemented using a wide variety of form factors, including any of the form factors shown and described herein or another form factor.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Conjunctions, such as "and," "or" are used interchangeably and are intended to encompass any one element, combination, or entirety of elements to which the conjunction refers.

Depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

The multi-source audio amplification and ear protection devices described herein may comprise software, firmware, hardware, or any combination(s) of software, firmware, or hardware suitable for the purposes described herein. Various disclosed and illustrated modules may be implemented as software and/or firmware on a logic circuitry, processor, microcontroller, ASIC/FPGA, or dedicated hardware. Software and other modules may reside remotely from a multi-source audio amplification and ear protection device, such as on personal computers, computerized tablets, PDAs, and other devices suitable for the purposes described herein, such as remote control of a multi-source audio amplification and ear protection device. Software and other modules may be accessible via local memory, via a network, or via other means suitable for the purposes described herein. User interface components described herein may comprise buttons, knobs, wheels, switches, touchscreen interfaces, and other suitable interfaces.

Computer program instructions may be stored in a computer-readable memory that can direct a computer or other programmable data processing apparatus to operate in a particular manner, thereby aiding in controlling a multi-source audio amplification and ear protection device.

The processing of the various components of the illustrated systems can be distributed across multiple logic circuits, processors, and other computing resources. In addition, two or more components of a system can be combined into fewer components. Various components of the illustrated systems can be implemented in one or more virtual machines, rather than in dedicated computer hardware systems. Moreover, in some embodiments the connections between the components shown represent possible paths of data flow, rather than actual connections between hardware. While some examples of possible connections are shown, any of the subset of the components shown can communicate with any other subset of components in various implementations.

While certain embodiments of the inventions have been described, these embodiments have been presented by way of example only, and are not intended to limit the scope of the disclosure. For example, while many of the headset embodiments and the growth band described above are described in connection with their use by an infant, one of skill in the art will recognize that the headsets and growth band can be sized to accommodate larger head sizes, such as the head of a school age child, an adolescent, an adult, or someone with an injured skull (e.g., due to surgery) over whose head conventional headsets do not fit properly. Therefore, the concepts described herein can be applicable to a variety of users and are not limited to use by infants. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A headset system, comprising:
   a headset comprising a left ear speaker, a right ear speaker and a headband that interconnects the left and right ear speakers; and
   a fabric band comprising a pair of straps and a central band portion, the pair of straps attached to opposite ends of the central band portion, each of the pair of straps extending between a first end of the strap and a second end of the strap and attached to the central band portion at a location along the strap between the first and second ends, the pair of straps configured to removably wrap at least partially about the headband at two locations of the headband to couple the fabric band to the headband so that the central band portion suspends below the headband with an adjustable spacing between the headband and the central band portion, so that the central band portion is disposed between the headband and a user's head when in use.

2. The system of claim 1 wherein the band is configured to fill a space between the headband and the user's head when in use to facilitate the secure and stable fit of the headset over the user's head to accommodate the user's growing head.

3. The system of claim 1, wherein the left ear speaker is supported by a left ear cup and the right ear speaker is supported by a right ear cup.

4. The system of claim 3, wherein the band is configured to facilitate the fitting of the headset on the user's head so that the left and right ear cups are positioned on the user's ears.

5. The system of claim 1, wherein the straps are removably coupled to the headband with hoop and loop fasteners.

6. The system of claim 1, wherein the central band portion and the pair of straps fabric band forms generally H-shape when the fabric band is laid generally flat.

7. The system of claim 1, wherein the central band portion comprises a resilient material that cushions the headband on the user's head.

8. The system of claim 1, wherein the central band portion has a width generally equal to a width of the headband.

9. The system of claim 1, wherein the headset provides passive noise suppression.

10. The system of claim 1, wherein the headset comprises a computer readable memory and has one or more pre-recorded sounds saved on the memory, the headset being actuatable to play the one or more pre-recorded sounds.

11. The system of claim 1, wherein the headset comprises electronics configured to filter out ambient sounds above a predetermined decibel level.

12. An infant headset kit, comprising:
    a headset comprising a left ear speaker, a right ear speaker and a headband that interconnects the left and right ear speakers; and
    at least one band comprising at least one strap and a central band portion, the strap attached to the central band portion, extending between a first end of the strap and a second end of the strap, and attached to the central band portion at a location along the strap between the first and second ends, the strap configured to releasably couple the band to the headband by removably wrapping around the headband, so that the central band portion suspends below the headband with an adjustable spacing between the headband and the central band portion, so that the central band portion is disposed between the headband and an infant's head when in use.

13. The kit of claim 12, wherein the left ear speaker is supported by a left ear cup and the right ear speaker is supported by a right ear cup.

14. The kit of claim 12, wherein the at least one band comprises a plurality of bands.

15. The kit of claim 12, wherein at least two of the plurality of bands have a central band portion of different thickness.

16. The kit of claim 12, wherein the at least one band is made of fabric.

17. The kit of claim 12, wherein the at least one band is reversible.

18. The kit of claim 12, wherein the headset provides passive noise suppression.

19. The kit of claim 12, wherein the headset has one or more pre-recorded sounds saved in a memory of the headset, the headset being actuatable to play the one or more pre-recorded sounds.

20. The kit of claim 12, wherein the headset comprises electronics configured to filter out sounds above a predetermined decibel level.

21. A headset system, comprising:
a headset comprising a left ear speaker, a right ear speaker and a headband that interconnects the left and right ear speakers; and
a band comprising at least one strap and a body portion, the strap configured to removably couple the band to the headband by removably wrapping around the headband, so that the body portion of the band suspends below the headband with an adjustable spacing between the headband and the body portion of the band, and is disposed between the headband and a user's head when in use,
wherein the body portion of the band comprises a compressible, resilient material.

* * * * *